Sept. 15, 1936. J. W. COOK Plant Pat. 192
ROSE BUSH
Filed Aug. 20, 1935
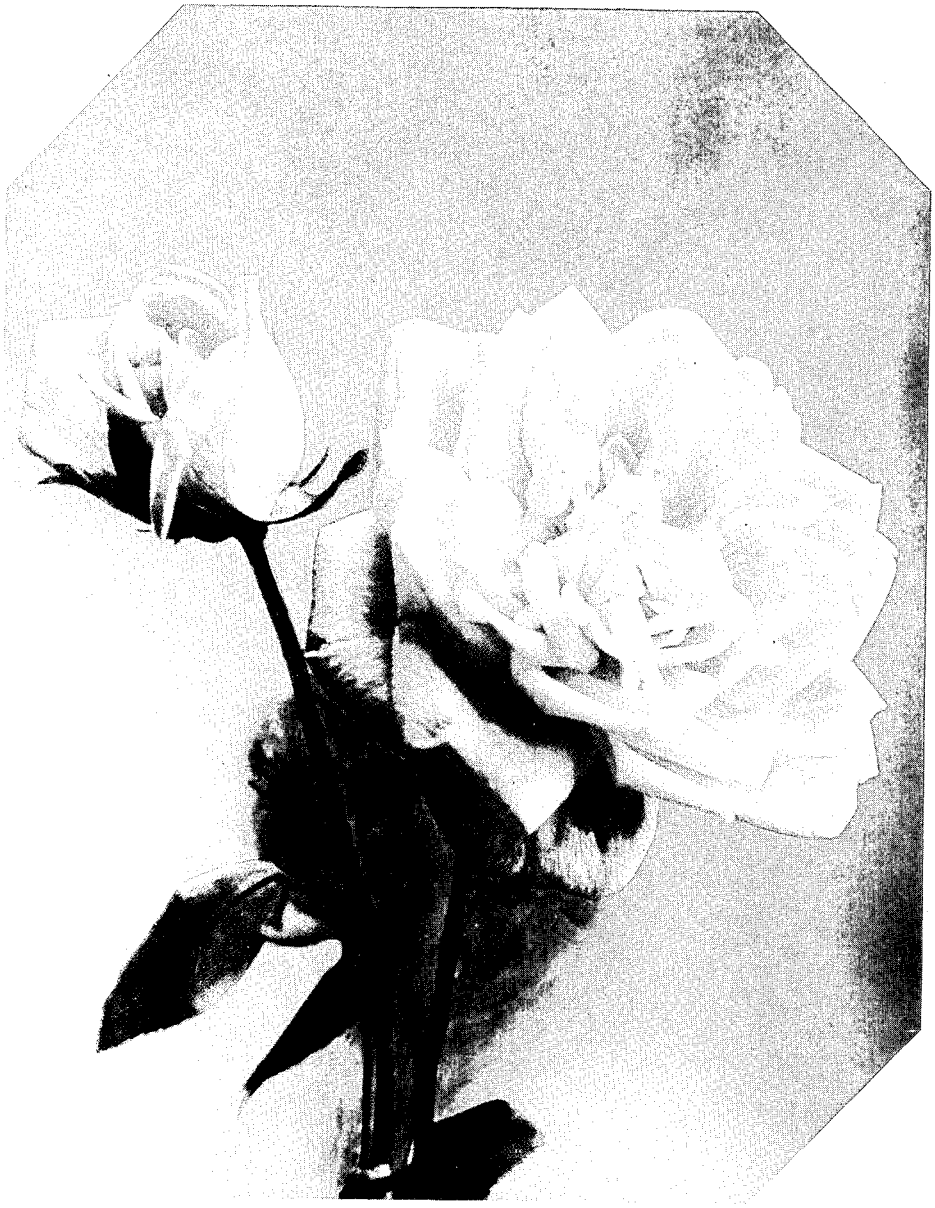
INVENTOR
Joseph William Cook
By Albert Rosenberg
Attorney 278

Patented Sept. 15, 1936

Plant Pat. 192

UNITED STATES PATENT OFFICE

192

ROSE BUSH

Joseph William Cook, Baltimore, Md., assignor to The John Cook, Incorporated, Baltimore, Md., a corporation of Maryland Application August 20, 1935, Serial No. 36,999

1 Claim. (Cl. 47—61)

My creation relates to rose culture and the method of creating the new rose was by crossing two known species of rose blooms by fertilizing one type of bloom with the pollen of the other type of bloom, the resulting seeds eventually growing the new rose bush and producing the most delicately tinted fragrant new rose buds and blooms with numerous petals.

My new rose is cream tinted delicately suffused with pink in the center; it has from sixty to sixty-five petals and sometimes more or less, varying with the seasons.

I produced or created the new rose by crossing a Souvenir De Claudius Pernet rose bloom, with a pink rose bloom known to the trade as the My Maryland rose.

To fertilize the pistils of the pink bloom of My Maryland rose, I first remove the stamens carrying the pollen from the said rose bloom before the pollen has been able to develop; then I take the stamens carrying the pollen from the Souvenir De Claudius Pernet rose bloom and insert pollen as close as possible to the pistils in the pink bloom of My Maryland rose bloom.

This cross-fertilization eventually produces the seeds from which I have developed or created the new rose bush and the new blooms.

To produce the said new rose required about four years of efforts, yielding the cream tinted buds and blooms suffused with pink in the center and distinguishable from other rose blooms, and having a delightful fragrance.

The rose buds grow from two to two and one-half inches long; the rose when in full bloom measures from three to three and one-half inches across, sometimes grows larger.

The flowers are hardy and long lived, appearing fresh fully one week after cutting from the rose bush plants. The new rose can be grown from cuttings from my new rose bush in the manner similar to the propagation of other rose bushes.

The following is a brief technical description of my new rose and plant;

*Parentage.*—Seedling from My Maryland rose. Pollen parent Souvenir De Claudius Pernet rose, both hybrid tea hybrid roses.

*Flower.*—Blooming habit is recurrent—continuous. Bud size is very large, the form of ovoid, and not affected by wet or hot weather; the color when sepals first divide, are rose-pinkish cream, with slight cadmium or canary shading at the base of the petals; there is a decided increase in the cream color as the bud opens; more and more so as the bloom comes to full growth. The inside of the petals are a cream color reflecting the canary or cadmium shading, giving the appearance of a changeable-color effect on the inside of the petals. The cream color is nearly 9-D-2 page 41 of Maerz and Paul, and the general effect nearly pale pinkish cinnamon (Ridgway XXIX-15'' f) with a yellowish cast. The delicate shade of pink, effected by reflection of petals against and through one another, is not exactly found in any color standard; it makes the appearance of being flushed with pink. The sepals are serrated, but stand at approximately right angles when the rose is in full bloom, curving and twisting upwards and away from the petals and calyx. The peduncle is long, light green color and medium heavy. The calyx is of the usual shape, but not large, the substance of the plant growing into the numerous petals instead of into the calyx, in this rose. The bud opens well and is not affected by adverse conditions. The size of this rose is very large when fully expanded, from four to four and one-half inches and sometimes five inches across the blooms. They are borne singly, but sometimes other buds grow on the same stem after the first bud nearly reaches maturity and is ready to open. The stems are long and strong. The form when first open is high center, and elongated and ovoid in shape.

*Permanence.*—The bud retains its shape until it is ready to open, and the rose is fully grown, it shows its numerous petals which number up to seventy or more petals.

*The color.*—The center of the opening bud is a rich pinkish cream, while the outer petals are a rich cream color which increases on both sides of the petals as the rose ages; on the inside of the petals there is reflected the cadmium or light canary color which appears to increase in shade towards the base of the petals.

*Discoloration.*—Tonality at the end of the first day, a rich pinkish cream, which increases the cream color on the second day and as the rose ages, but loses some of its pinkish shading; and as the rose reaches full blooming period after the third day, all of the pinkish tints vanish more or less into the full cream on all the petals, both inside and outside of the petals except the cadmium or canary shading which varies slightly with the aging of the rose, making this rose very distinctive.

The texture is substantial and not affected by hot or wet weather.

The appearance, inside is satiny and slightly reflective of the adjacent outside of the petals.

Outside is a pinkish cream shading towards the inner edge to light cadmium or canary color.

The form is rounding like most of the larger roses.

The arrangement is imbricated with numerous petaloids; some large and others varying in sizes. In its persistence, the rose holds well together to the last of its age. It is extra fragrant like the tea roses but more agreeable. Its permanence is vary lasting on the plant, and as a cut flower, the fragrance lasts a very long time.

The genital organs, comprise anthers which are not particularly prominent, and the pollen which is lemon yellow. The styles are loosely separated, of unequal length, medium heavy. Stigmas are yellow, and the ovaries are all inclosed in the calyx.

*Fruit.*—Variety is fertile with its own pollen, form is ovoid.

Aspect is smooth and the color at maturity is yellow. The sepals are caducous; curved and twisting. The plant form is bushy, and its growth is vigorous in branching. The leaflets at the flower stem vary in numbers, sometimes there are three leaflets and other flower stems may have four or five, at other places there appear the number usual with hybrid teas, sometimes five and in other places seven. The size is about usual, the outer leaflet being much larger than the others on the rachis.

The quantity of the leaves is about as usual with hybrid tea rose bushes, their color being dark green, the new foliage on the upper surface is darker than the underside; their ribs are ordinary and smooth; their shape is long and ovoid, pointed at the outer end. Their texture shows the upper side to be smoother than the underside, their edges being serrated with small serrations, the leaf stems green, with the underside smooth. My rose bush is very resistant to disease. The color of the new wood is medium light green and the bark is smooth, the old wood being darker than the new wood, and the bark is smooth.

The quantity of the thorns on the main stalks is about as usual with hybrid teas, and on the laterals is about the same as found on most rose bushes in this class. Their form has a broad base, not extra long, curving downwards. Their positions are regular and irregular. There are few prickles on the main stalks as well as on the laterals, with their color a medium light green, but the thorns are good size. The needles on the thorns are long and curving downwards and are very sharp. The term "needles" is meant to describe the tips of the thorns.

Having described my new rose and rose bush, what I claim is:

A new rose substantially as herein disclosed, characterized by a bud with many petals, said petals tinted cream-colored.

JOSEPH WILLIAM COOK.